United States Patent [19]

Wilson

[11] Patent Number: 4,921,950

[45] Date of Patent: May 1, 1990

[54] PREPARATION OF 3'AZIDO-3-'-DEOXYTHYMIDINE

[75] Inventor: Jeffrey D. Wilson, Durham, N.C.

[73] Assignee: Burroughs Wellcome Co., Research Triangle Park, N.C.

[21] Appl. No.: 204,496

[22] Filed: Jun. 9, 1988

[51] Int. Cl.$^5$ .................. C07H 17/00; C07H 15/04
[52] U.S. Cl. .................................. 536/23; 536/1.1; 536/116; 536/122
[58] Field of Search .................. 536/23, 24, 1.1, 116, 536/122

[56] References Cited

U.S. PATENT DOCUMENTS 4,604,382 8/1956 Lin et al. .................. 536/203

FOREIGN PATENT DOCUMENTS 0196382 10/1986 European Pat. Off. .
0199451 10/1986 European Pat. Off. .

OTHER PUBLICATIONS

W. Ostertag, et al., Proc. Nat. Acad. Sci. USA, vol. 71, No. 12, pp. 4980–4985, Dec. 1974.
C. D. Anderson, et al., J. of Amer. Chem. Soc., vol. LXXX, 1958, pp. 5247–5252, Synthesis and Ammonolysis of Methyl 2,3-Anhydro-D-Ribofuranoside.
J. of the Amer. Chem. Soc., vol. 108, No. 11, 1986, pp. 3115–3117.
J. Carbohydrates, Nucleosides, Nucleotides, 2(2), 147–151, (1975).
Synthesis of Some Nucleotides Derived from 3'-Deoxythymidine, vol. 8, No. 12, Dec., 1969.
J. Med. Chem. 1980, 23, 1088–1094, Nucleosides, 116.
J. Med. Chem. 1984, 27, 986–990, Pyrazolo[4,3-d]-pyrimidine Nucleosides, Synthesis and Antiviral Activity of 1-B-D-Ribofuranosyl -3-methyl-6-substituted-7H-pyrazolo[4,3-d]pyrimidin-7-ones, Pier Giovanni Baraldi et al.
Anderson et al., J.A.C.S., vol. 80 (1958), pp. 5247–5252.
Horwitz et al., J. Org. Chem. 29, pp. 2076–2078 (1964).
Glinski et al., J. Org. Chem. 38 (1973), pp. 4299–4305.
Lin et al., J. Med. Chem. 1978, vol. 21, No. 1, pp. 109–112.
Yarchoan et al., The Lancet, 1986, pp. 575–580.

*Primary Examiner*—Cecilia Shen
*Attorney, Agent, or Firm*—Donald Brown

[57] ABSTRACT

This invention relates to a new synthetic process for the manufacture of zidovudine from the starting material D-xylose involving:
(i) Conversion of D-xylose to a 1-(β-D-xylofuranosyl)thymine derivative:
(ii) 2'-Deoxygenation of the thymaine derivative; and
(iii) 3'-Azidation of the 2'-deoxy compound.

6 Claims, No Drawings

PREPARATION OF 3'AZIDO-3-'-DEOXYTHYMIDINE

The present invention relates to a novel process for the preparation of 3'-azido-3'-deoxythmidine and to intermediates of use in such a process.

The preparation of 3'-azido-3'-deoxythymidine was first described by J. P. Horwitz et al., J. Org. Chem., 29, 2076–2078, 1964, and later for example by R. P. Glinski et al., J. Org. Chem, 38, 4299–4305, 1973 and T-S Lin et al., J. Med. Chem., 21 109–112 1978. More recently, 3'-azido-3'-deoxythymidine has been discovered to have a potent antiviral activity against the human immunodeficiency virus (HIV), and has been reported to be of potential value for the therapeutic treatment of acquired immune deficiency syndrome (AIDS) (R. Yarchoan et al., The Lancet, 1 (8481), 575–580, Mar. 15, 1986). Following further extensive clinical investigation this compound has been found to be of therapeutic benefit in the treatment of AIDS and AIDS-related complex (ARC). 3'-Azido-3'-deoxythymidine (otherwise named 1-(3'-azido-2'-3'-dideoxy-D-erythro-pentofuranosyl)-thymine) has recently been given the approved named zidovudine.

In view of the demand for relatively large quantities of zidovudine to fulfil clinical testing requirements and to meet other demands for the compound, considerable effort has been devoted towards ensuring adequate supplies of the compound on an industrial scale. A major difficulty that has been encountered in the commercial manufacture of zidovudine is that previously reported methods for the preparation of zidovudine (on a laboratory scale) have involved the use of thymidine as a starting material or intermediate. However, thymidine is a relatively expensive material and its commercial availability is relatively limited, which consequently limits the supply of zidovudine when prepared by previously reported methods.

We have therefore investigated alternative routes of synthesis for zidovudine starting from other, less expensive and more readily available, starting materials. As a result of considerable research and development, we have now discovered a synthetic route for zidovudine that uses, as a starting material, D-xylose which is a relatively inexpensive and readily commercially available starting material, thus avoiding the use of thymidine.

The new synthetic route is characterised by a sequence of key steps involving certain novel intermediates for example novel 5'-methoxy carbonyl-protected derivatives described in more detail below. These intermediates may then be converted to zidovudine by a series of steps essentially involving 2'-deoxygenation (which may be photolytic in nature); introduction of a leaving group at the 3'-position of the sugar residue and replacement of said leaving group by an azido group.

The overall synthetic route will be described in relation to the key steps referred to above which essentially involve (i) conversion of D-xylose to a 1-(β-D-xylofuranosyl)thymine derivative, (ii) 2'-deoxygenation of the thymine derivative; and (iii) 3'-azidation and 5'-deprotection of the 2'-deoxy compound.

Thus, the key steps, each of which represents a feature of the present invention, comprise:

(i) Conversion of D-xylose to 1-(β-D-xylofuranosyl)thymine derivative (a) treating D-xylose, i.e.

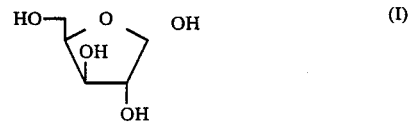

with a selective hydroxy blocking agent to form a compound of formula (II)

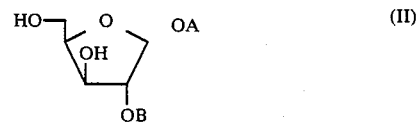

in which A and B each represent a hydroxy blocking group or together form a single such group serving to block the 1- and 2-hydroxy groups;

(b) treating a compound of formula (II) with further hydroxy blocking agents which selectively block the 5- and/or 3-hydroxy groups;
  (i) optionally treating the resulting compound with an agent capable of deblocking the 1- and 2-hydroxy groups; or alternatively
  (ii) treating the resulting compound with an agent serving to introduce a leaving group at the 3-position of the sugar ring and optionally replacing any combined groups blocking the 1- and 2-hydroxy groups with single such blocking groups or a single group blocking the 1-hydroxy group, the 2-hydroxy group being optionally blocked by a photolytically reduceable group; and then
  (iii) optionally introducing a leaving group at the 1-hydroxy position of the sugar ring.

(c) reacting the resulting compound with a thymine derivative of formula (III)

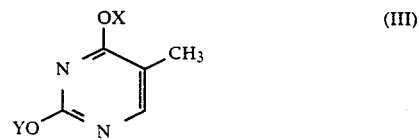

(wherein X and Y each represent an activating group), to form a compound of formula (IV)

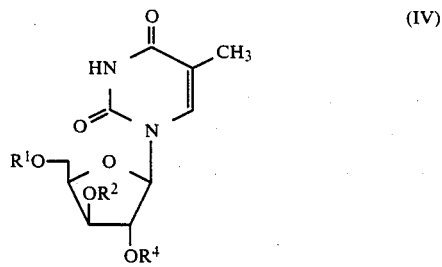

(wherein $R^1$ is a hydroxy blocking group, $R^2$ is a leaving group, or $R^1$ and $R^2$ are individual hydroxy blocking groups and $R^4$ is hydrogen or a hydroxy blocking group preferably a photolytically reduceable group).

(ii) 2'-deoxygenation of the thymine derivative (d) (i) optionally deblocking the 3' and 5'-hydroxy groups and reblocking with alternative blocking groups (wherein $R^4$ is a non-photolytically reduceable hydroxy blocking group, treating a compound of formula (IV) with an agent to remove the 2'-hydroxy blocking group), then treating the 2'-hydroxy compound with an agent serving to provide a photolytically or non-photolytically reduceable group at the 2'-position of the sugar moiety directly, or by:
(1) introducing a leaving group at the 2'-position of the sugar moiety;
(2) cyclising the compound to form a 2',2-anhydro derivative and either
    (a) opening the ring to give a compound of formula (V)a or (V)b;

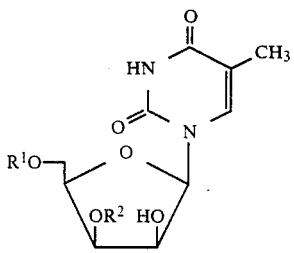

(V)a

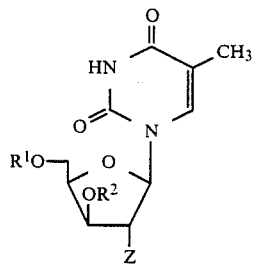

(V)b (wherein $R^1$ and $R^2$ are as hereinbefore defined and Z is a photolytically or non-photolytically reducible group) and introducing a photolytically reducible group at the 2'-position of the sugar ring of structure (V)a; or
    (b) introducing a non-photolytically reducible group at the 2'-position of the sugar ring, and reducing to form a compound of formula (VI) below.

(d) (ii) treating a compound of formula (IV) wherein $R^4$ is a photolytically reduceable group or a compound from (d) (i) above to deoxygenate the 2'-position sugar moiety to form a compound iof formula (VI);

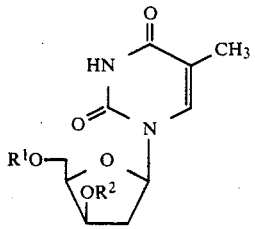

(VI)

(wherein $R^1$ and $R^2$ are as hereinbefore defined)

(iii) 3'-Azidation of the 2'-deoxygenated 1-(β-D-xylofuranosyl)thymine derivative (e) reacting the compound of formula (VI) with an agent serving to introduce an azido group at the 3'-position in the erythro configuration to form a compound of formula (VII)

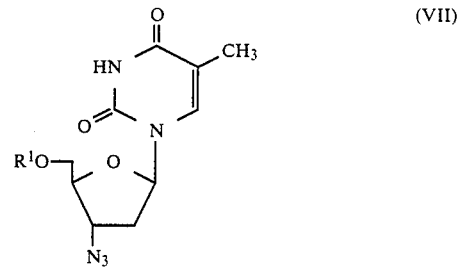

(VII)

(in which $R^1$ is as hereinbefore defined) and (f) removing the 5'-hydroxy protecting group from the compound of formula (VII) to form zidovudine.

The above procedures for the preparation of zidovudine from D-xylose are hereinafter described in more detail.

With regard to stage (a), the 1- and 2-hydroxy groups of xylose may be protected as a ketal (e.g. acetonide) blocking group, for example by treatment of D-xylose with an appropriate agent such as acetone.

With regard to stage (b), a single 5'-blocking group may be an alkoxycarbonyl group e.g. methoxycarbonyl, the compound of formula (II) being advantageously reacted with an appropriate chloride, e.g. methoxycarbonyl chloride, preferably in the presence of a base such as pyridine.

With regard to stage (b) option (ii) the leaving group may be an organosulphonyloxy (e.g. methanesulfonyloxy, trifluoromethane sulphonyloxy or p-toluenesulphonyloxy) group, the compound of formula (II) being advantageously reacted with an appropriate chloride or anhydride, e.g. methanesulphonyl chloride, preferably in the presenc of a base such as triethylamine, and conveniently in an organic solvent such as dichloromethane. The 1- and 2-hydroxy protecting groups are preferably acyl protecting groups, particularly acetyl or benzoyl protecting groups, the compound of formula (II) being reacted with an appropriate acylating agent such as acetic anhydride in acetic acid, for example in the presence of a mineral acid such as sulphuric acid. The preparation of an analogous compound is also described in J. Am. Chem. Soc., 1958; 80, 5247.

A photolytic reduceable group which is advantageously a benzoate group or substituted benzoate group (e.g. 4-chlorobenzoate or 3-trifluoromethyl benzoate) may be introduced at the 2-hydroxy position of the sugar moiety containing a single group blocking the 1-hydroxy by treatment with an appropriate acid halide (e.g. chloride) or anhydride at ambient temperature in the presence of an aprotic base such as pyridine.

With regard to stage (b) (iii) the leaving group may be an acyl group particularly acetyl and may be introduced at the 1-hydroxy position of the sugar ring by treatment with an acylating agent such as acetic anhydride in acetic acid.

With regard to stage (c) the resulting compound is reacted with a compound of formula (III) in which X and Y are advantageously trialkylsilyl (e.g. trimethylsilyl) groups, the reaction being effected in the presence of a Lewis Acid (e.g. stannic chloride or trimethylsilyl trifluoromethanesulphonate), preferably in an organic solvent such as methylene dichloride or acetonitrile.

With regard to stage (d) option (i) wherein $R^4$ of compound of formula (IV) is a non-photochemical hydroxy-protecting group, the removal of the 2'-hydroxy blocking group is advantageously effected by treatment of the compound of the formula (IV) under acidic conditions, for example using anhydrous methanolic hydrochloric acid. The 2'-reduceable functional group may be introduced directly as a halo radical in particular a bromo radical using a dialkyl azodicarboxylate, a trialkyl or tri-aryl phosphine (eg. $Ph_3P$) in a aprotic solvent (eg. DMF) and a brominating agent eg. an alkaline earth metal bromide such as lithium bromide (LiBr).

Alternatively, the reduceable group may be introduced by the sub-stages (i) to (iii) in stage (d) as follows:

(1) The leaving group is advantageously an organosulphonyloxy group (e.g. a methanesulphonyloxy, trifluoromethanesulphonyloxy or p-toluenesulphonyloxy) group, the compound being treated with an appropriate sulphonyl halide (e.g. chloride), as described for stage (c).

(2) Cyclisation of the compound is conveniently effected by treatment with a base such as potassium carbonate, for example in a solvent such as acetonitrile, preferably at an elevated temperature e.g. reflux temperature.

2 option (b)

The reduceable functional group is preferably a halo radical, for example a chloro or iodo radical, but preferably a bromo radical, in which case, the compound is reacted with a brominating agent such as lithium bromide. Alternative reduceable groups include those of formula —CS.R (in which R represents an imidazolyl, $C_{1-4}$ alkoxy (e.g. methoxy), aryloxy (e.g. phenoxy) or $C_{1-4}$ alkylthio group. The reduction of the compound is preferably effected using a reducing agent such as tributyltin hydride, particularly in the presence of azobisisobutyronitrile as a catalyst, preferably in an organic solvent such as toluene.

With regard to stage (d) option (ii) wherein $R^4$ of a compound of formula (IV) is a photochemical group, 2'-deoxygenation is achieved by photolytic removal of the photochemical group carried out by irradiating the compound of formula (IV) with a high pressure mercury lamp having a pyrex or uranium filter, in the presence of an electron transfer agent such as N-methylcarbazole or N-ethylcarbazole in an aqueous/organic solvent system such as water/THF (1:10) or water/isopropanol (1:10) at about room temperature under an inert atmosphere such as nitrogen. The process is described in J. Amer. Chem. Soc. 1986 Vol 108 Page 3115.

In stage (f), the azido group is introduced at the 3'-position by treatment of the compound of formula (VI) with an appropriate agent e.g. an alkali metal azide such as sodium azide e.g. in an organic solvent such as dimethylformamide.

In stage (g) the removal of the 5'-protecting group of formula (VII) is advantageously effected by treatment with an appropriate base e.g. sodium bicarbonate.

It should be appreciated that the invention is concerned not only with the overall synthetic route outlined above for the conversion of D-xylose into zidovudine, but also with the individual reaction stages. The overall synthetic route and also its novel individual stages, alone or in combination, each represent further features of the invention together with the novel intermediates referred to below.

(a) The novel compounds of formula (IV) wherein: $R^1$ is methoxycarbonyl, $R^2$ is mesylate and $R^4$ is acetyl, hydrogen or trifluoromethylbenzoyl;

(b) The novel compounds of stage (b) wherein: the 5-hydroxy blocking group is methoxycarbonyl, the 3-leaving group is mesyl the 2-reduceable group is trifluoromethylbenzoyl and the 1-hydroxy blocking group is methyl or acetyl;

(c) The novel compounds of formula (VI) wherein: $R^1$ is methoxycarbonyl and $R^2$ is mesyl;

(d) The novel compounds of stage (d) wherein:
 (i) the 5'-hydroxy blocking group is methoxycarbonyl and 2'- and 3'-leaving groups are mesyl;
 (ii) the 5'-hydroxy blocking group is methoxycarbonyl, the 3'-leaving groups is mesyl and the 2'-position forms a cyclic link with the 2-position of the base;
 (iii) the 5'-hydroxy blocking group is methoxycarbonyl, the 3'-leaving group is mesyl and the 2'-reduceable group is bromo;

(e) The novel compound of formula (VII) wherein $R^1$ is methoxycarbonyl.

(f) The use of each and every compound listed in (a)–(e) above in the synthesis of zidovudine particularly from the starting material D-xylose.

(g) A compound as listed in (a)–(e) above for use in the synthesis of zidovudine particularly from the starting material D-xylose.

(h) A process for the preparation of zidovudine from a compound of formula (VII) wherein $R^1$ is methoxycarbonyl.

(i) A process for the preparation of zidovudine involving photochemical 2'-deoxygenation of a compound of formula (IV) wherein $R^4$ is a photolytic group.

(j) A process for the preparation of zidovudine from D-xylose involving stages (a)–(g) above, and each and every novel stage thereof.

The following Examples illustrates the present invention.

EXAMPLES FOR ALTERNATIVE A

Photochemical Method

Example A1

Methyl 3-O-mesyl-5-O-(methoxycarbonyl)-2-O-(m-trifluoromethylbenzoyl)-D-xylofuranoside A flame dried 250 ml flask equipped with an addition funnel, magnetic stirrer and nitrogen inlet was charged with methyl 3-O-mesyl-5-O-(methoxycarbonyl)-D-xylofuranoside (5.84 g, 19.4 mmoles) (C. D. Anderson, L. Goodman and B. R. Baker, J. Am. Chem. Soc. 1958, 80, 5247) and anhydrous pyridine. The solution was cooled in an ice bath and 3-(trifluoromethyl)-benzoyl chloride (5.27 g, 25.3 mmoles) was added dropwise over 10 min. After the addition was complete the ice bath was removed and the reaction was continued 24 hours at ambient temperature. The mixture was poured into ice water (400 mL) and the aqueous solution extracted with ether (2×250 mL). The combined ether extracts were washed with 400 mL of 1.2NHCl and 400 mL of 10% aqueous $NaHCO_3$. The solvent was removed by rotary evaporation and the residual oil was purified by flash chromatography (3-inch diameter column containing 18 inches of flash silica gel). The column was eluted with 1:1/ethyl acetate:hexanes while collecting 200 mL fractions. Fractions 12-15 contained pure product and these fractions were concentrated in vacuo to afford 8.92 g (97.3%) of methyl 3-O-mesyl-5-O-(methoxycarbonyl)-2-O-(m-trifluoromethylbenzoyl)-D-xylofuranoside as a colourless oil containing an approximately equal mixture of α and β anomers. $^1$H NMR (CDCl$_3$) δ3.09 and 3.19(s, 3H, OCH$_3$), 3.34 and 3.37(s, 3H, SO$_2$CH$_3$), 3.79(s, 3H, OCO$_2$CH$_3$), 4.4-4.9(m, 3H, C-4H and C-5H), 5.1-5.6(m, 3H, C-1H, C-2H and C-3H) and 7.5-8.5 (m, 4H, ArH); TLC R$_f$=0.77 and 0.84, silica gel, CHCl$_3$:CH$_3$OH/90:10.

Example A2

1-O-Acetyl-3-O-mesyl-5-O-(methoxycarbonyl)-2-O-(m-trifluoromethylbenzoyl) D-xylofuranose A 250 mL flask equipped with a nitrogen inlet, magnetic stirrer and addition funnel was charged with methyl-3-O-mesyl-5-O-(methoxycarbonyl)-2-O-(m-trifluoromethylbenzoyl)-D-xylofuranoside (19.0 g, 40.2 mmoles) from Example A1, acetic acid (170 mL) and acetic anhydride (25 mL). The solution was cooled to 10° C. in an ice bath and sulfuric acid (15 mL) was added dropwise over 20 minutes. After the addition was complete the ice bath was removed and the reaction was continued for 16 hours at ambient temperature. The reaction solution was poured into a solution of ice water (1.1 L) and methanol (0.1 L). Stirring was continued an additional 30 minutes and the aqueous solution was extracted with chloroform (3×250 mL). The combined chloroform extracts were carefully washed with 10% aq. NaHCO$_3$ (3×700 mL) and the solvent was removed in vacuo to a constant weight affording 19.6 g (97.4%) of 1-O-acetyl-3-O-mesyl-5-O-(methoxycarbonyl)-2-O-(m-trifluoromethylbenzoyl)-D-xylofuranose as an approximately equal mixture of anomers: $^1$H NMR (CDCl$_3$) δ2.13 and 2.19(s, 3H, OCOCH$_3$), 3.13 and 3.21(s, 3H, SO$_2$CH$_3$), 3.78 and 3.79(s, 3H, OCO$_2$CH$_3$), 4.2-4.9(m, 3H, C-4H and C-5H), 5.2-5.6(m, 2H, C-2H and C-3H), 6.35(s, 1H, C-1, β-anomer), 6.57(d, J=4.1 Hz, C-1H, α-anomer), 7.5-8.2(m, 4H, ArH).

Example A3

1-(3-O-Mesyl-5-O-(methoxycarbonyl)-2-O-(m-trifluoromethylbenzoyl)-β-D-xylofuransoyl)thymine A flame dried 250 mL flask equipped with a magnetic stirrer, nitrogen inlet and additional funnel was charged with 1-O-acetyl-3-O-mesyl-5-O-(methoxycarbonyl)-2-O-(m-trifluoromethylbenzoyl)-D-xylofuranose (19.4 g, 38.8 mmoles) from Example A2, 2,4-bis(trimethylsilyl)thymine (14.7 g, 54.3 mmoles) and methylene chloride (200 ml). Stannic chloride (62.4 mmoles, 1M in methylene chloride) was added dropwise over 25 minutes and the solution was stirred for 20 hours at room temperature. The solution was carefully poured into 15% aqueous NaHCO$_3$ (1.2 L) and the aqueous layer extracted with methylene chloride (3×300 mL). The combined organic extracts were washed with 10% aqueous NaHCO$_3$ (200 mL) and concentrated by rotary evaporation. The residual solid was purified by flash chromatography (70:30/ethyl acetate:hexanes) affording 12.8 g (52.0%) of 1-(3-O-mesyl-5-O-(methoxycarbonyl)-2-O-(m-trifluoromethylbenzoyl)-β-D-xylofuranosyl)thymine: mp: 94°-96° C.; TLC R$_f$=0.61, silica gel, CHCl$_3$:CH$_3$OH/90:10;

Example A4

1-[2-Deoxy-3-O-mesyl-5-O-methoxycarbonyl-β-D-threo-pentofuranosyl]thymine

A 500 mL pyrex photochemical reaction vessel equipped with a nitrogen inlet, magnetic stirrer, reflux condenser, quartz immersion well and a 450 watt medium pressure mercury-vapor immersion lamp surrounded by a uranium absorption sleeve was charged with 90% aqueous isopropyl alcohol (500 mL), N-methyl carbazole (1.46 g, 8.05 mmoles) and 1-(3-O-mesyl-5-O-(methoxycarbonyl)-2-O-(m-trifluoromethylbenzoyl)-β-D-xylofuranosyl)thymine (3.80 g, 6.71 mmoles) from Example A3. After bubbling nitrogen through the solution for 45 minutes the solution was photolyzed for 20 hours. The solvent was concentrated to a 50 mL volume by rotary evaporation and the remaining liquid was diluted with chloroform (300 mL). The organic solution was washed with 10% aqueous NaHCO$_3$ (2×200 ml) and the solvent was removed by rotary evaporation. The residual oil was purified by flash chromatography (3-inch diameter column containing 15 inches of flash silica gel). The column was eluted with 95:5/CHCl$_3$:CH$_3$OH while collecting 125 mL fractions. Fractions 15-19 contained pure product and these fractions were concentrated in vacuo affording 1.75 g (68.9%) of 1-[2-deoxy-3-O-mesyl-5-O-methoxycarbonyl-β-D-threo-pentofuranosyl]thymine as a white crystalline solid. mp: 70°-72° C.; TLC R$_f$=0.51. Silica gel, CHCl$_3$: CH$_3$OH/90/10

CHEMICAL METHOD

Example A5

2'-O-Acetyl-3'-O-mesyl-5'-O-(methoxycarbonyl)-1-β-D-xylofuranosylthymine

A flame-dried 250-ml round bottom flask equipped with a magnetic stirrer, addition funnel and nitrogen inlet was charged with 1,2-di-O-acetyl-3-O-mesyl-5-O-methoxycarbonyl-D-xylofuranose (5.0 g, 13.4 mmoles), prepared as described by C. D. Anderson et al (J. Am. Chem. Soc. 1958, 80 5247; 5.00 g) and 2,4-bistrimethylsilyl)thymine (5.43 g, 20.1 mmoles) in 100 mL of methylene chloride. Stannic chloride (1M in methylene chloride; 20 mL) was added dropwise over 30 minutes and the solution was stirred an additional 18 h at room temperature. The solution was diluted with 100 mL of methylene chloride, transferred to a separatory funnel and carefully washed with 2×150 mL portions of 10% aq. sodium bicarbonate. The organic solution was filtered through celite and concentrated by rotary evaporation. The crude product was purified by flash chromatography (97:3/CHCl$_3$:CH$_3$OH) affording 3.85 g (65.8%) of 2'-O-acetyl-3'-O-mesyl-5'-O-(methoxycarbonyl)-1-β-D-xylofuranosylthymine: mp 87°-89° C.; $^1$H NMR (CDCl$_3$) δ1.94 (d, j=1.18 Hz, 3H, C-5CH$_3$), 2.15 (s, 3H, COCH$_3$), 3.17 (s, 3H, SO$_2$CH$_3$), 3.83 (s, 3H, CO$_2$CH$_3$), 4.50 (m, 3H, C-4' and C-5'H), 5.14 (m, 1H, C-3'H), 5.25 (m, 1H, C-2'H), 6.09 (d, J=3.37 HZ, 1H, C-1'H), 7.32 (m, 1H, C-6H) and 8.64 (broad, 1H, NH); $^{13}$C NMR (CDCl$_3$) δ12.58, 20.53 38.49, 55.33, 64.17, 76.46, 79.36, 79.82, 87.27 112.01, 134.73, 150.48, 155.13, 163.74 and 169.69; TLC, R$_f$=0.59, silica gel, CHCl$_3$:CH$_3$OH/90:10.

Example A6

3'-O-Mesyl-5'-O-(methoxycarbonyl)-1-β-D-xylofuranosylthymine

Anhydrous methanolic HCl was prepared by adding acetyl chloride (4.42 g) dropwise to anhydrous methanol (0.125 l) at room temperature 2'-O-acetyl-3'-O-mesyl-5'-O-(methoxycarbonyl)-1-β-D-xylofuranosylthymine (3.50 g, 8.02 mmoles) from Example A5 was added and the resulting solution was stirred 3 days at ambient temperature. The solution was cooled 1 hour in an ice bath, the resulting precipitated solids collected by filtration and washed with 10 mL of prechilled methanol. The solids were dried 18 h in a vacuum at 50° C. affording 2.45 g (75.2%) of 3'-O-mesyl-5'-O-(methoxycarbonyl)-1-β-D-xylofuranosylthymine: mp=163°–166° C., $^1$H NMR (CDCl$_3$) δ1.91 (d, J=0.94 Hz, 3H, C-5 CH$_3$), 3.10 (s, 3H, SO$_2$CH$_3$), 3.49 (broad, 1H, OH), 3.83 (s, 3H, CO$_2$CH$_3$), 4.49–4.75 (m, 4H, C-2H, C-4'-H, C-5'-H), 5.13 (doublet of doublets, J=4.38 Hz and 3.04 Hz, 1H, C-3'-H), 5.84 (d, J=2.64 Hz, 1H, C-1'H), 7.50 (m, 1H, C-6H), and 10.01 (broad, 1H, NH); $^{13}$C NMR (DMSO-d$_6$) δ12.07, 37.58, 54.91, 65.10, 76.39, 76.75, 82.16, 88.43, 109.56, 135.34, 150.48, 154.75 and 163.56; TLC, R$_f$=0.53, silica gel, CHCl$_3$: CH$_3$OH/90:10; Elemental Analysis calcd C, 39.59; H, 4.60; N, 7.10. Found C, 39.41; H, 4.67; N, 7.01.

Example A7

3'-O-Mesyl-5'-O-(methoxycarbonyl)-1-β-D-xylofuranosylthymine

Sodium acetate (0.563 g, 6.87 mmoles) and hydroxylamine hydrochloride (0.477 g, 6.87 mmoles) were dissolved in pyridine (10 mL) in a 25 ml flask equipped with a magnetic stirrer and nitrogen inlet. The solution was stirred 30 minutes as room temperature followed by the addition of 2'-O-acetyl-3'-O-mesyl-5'-O-(methoxycarbonyl)-1-β-D-xylofuranosylthymine (1.0 g, 2.29 mmoles) from Example A5. After stirring 20 hours at room temperature the solution was poured into a solution of 50 mL of ethanol and 10 mL of acetone. The solution was filtered and concentrated by rotary evaporation. Residual pyridine was removed by concentration from an additional 40 mL of ethanol. The residual oil was triturated with 20 mL of ethanol at 0° C. for 30 minutes and the precipitated solids were collected by filtration and dried 18 hours in a vacuum oven at 50° C. affording 0.662 g (73.0%) of 3'-O-mesyl-5'-O-(methoxycarbonyl)-1-β-D-xylofuranosylthymine: mp=162°–165° C.; TLC R$_f$=0.53, Silica Gel, (CHCl$_3$: CH$_3$OH 90:10) The product was chromatographically and spectroscopically identical to material synthesized in Example A6.

Example A8

3'-O-mesyl-5'-O-(methoxycarbonyl)-1-β-D-xylofuranosylthymine

2'-O-Acetyl-3'-O-mesyl-5'-O-(methoxycarbonyl)-1-β-D-xylofuranosylthymine (1.0 g, 2.29 mmoles) from Example A5 was dissolved in a mixture of pyridine (8 mL) and acetic acid (2 mL). After stirring 48 hours at room temperature, the solution was poured into a solution of ethanol (50 ml) and of acetone (10 mL). The solution was concentrated by rotary evaporation and residual pyridine was removed by concentration from an additional 40 mL of ethanol. The residual oil was triturated with 20 mL of ethanol at 0° C. for 1 hour and the precipitated solids were collected by filtration and dried 18 hours in a vacuum oven at 50° C. affording 554 mg (61.3%) of 3'-O-mesyl-5'-O-(methoxycarbonyl)-1-β-D-xylofuranosylthymine: mp=162°–165° C.; TLC R$_f$=0.53 Silica Gel, (CHCl$_3$: CH$_3$OH 90:10)

The product was chromatographically and spectroscopically identical to material synthesized in Example A6.

Example A9

2'-Bromo-2'-deoxy-3'-O-mesyl-5'-O-(methoxycarbonyl)-1-β-D-xylofuranosyl thymine

A 25 mL flask equipped with an addition funnel, magnetic stirrer and nitrogen inlet was charged with 3'-O-mesyl-5'-O-(methoxycarbonyl)-1-β-D-xylofuranosylthymine (0.05 g, 1.27 mmoles) from Example A7, triphenylphosphine (0.663 g, 2.53 mmoles) and DMF (10 mL). A solution of diisopropyl azodicarboxylate (0.512 g, 2.53 mmoles) in DMF (1 mL) was added dropwise over 10 minutes and stirring was continued an additional 45 minutes. Lithium bromide (0.22 g, 2.53 mmoles) and sodium bisulfate monohydrate (0.349 g, 2.53 mmoles) were added and the suspension was heated at 110° C. for an additional 45 minutes. The suspension was cooled to room temperature, diluted with ethyl acetate and washed with 2×100 mL portions of water. Solvent was removed by rotary evaporation and the residual solids were purified by flash chromatography (96:4 CHCl$_3$:CH$_3$OH). The appropriate fractions were combined and concentrated in vacuo affording 0.459 g (79.0%) of 2'bromo-2'-deoxy-3'-O-mesyl-5'-O-(methoxycarbonyl)-1-β-D-xylofuranosylthymine: mp=86°–89° C.; TLC, R$_f$=0.77, Silica Gel, 90:10 CHCl$_3$:CH$_3$OH The product was chromatographically and spectroscopically identical to material synthesized in Example A12 below.

Example A10

2',3'-Di-O-mesyl-5'-O-(methoxycarbonyl)-1-β-D-xylofuranosylthymine

A flame dried, three necked 250 mL flask equipped with a magnetic stirrer nitrogen inlet and addition funnel was charged with 3'-O-mesyl-5'-O-(methoxycarbonyl)-1-β-D-xylofuranosylthymine (5.00 g, 12.7 mmoles) from Example A6, triethylamine (3.23 g, 31.9 mmoles) and methylene chloride (100 mL). The solution was cooled in an ice bath, a solution of methanesulfonyl chloride (3.05 g, 26.6 mmoles) in 5 mL of methylene chloride added dropwise over 20 minutes and stirring continued an additional 1 h. The solution was transferred to a separatory funnel, washed with 100 mL portions of water, 1.2N hydrochloric acid and 10% aqueous sodium bicarbonate and concentrated by rotary evaporation. The resulting crude solid was purified by flash chromatography (94:6; CHCl$_3$:CH$_3$OH) affording 4.31 g (72.0%) of 2',3'-di-O-mesyl-5'-O-(methoxycarbonyl)-1-β-D-xylofuranosyl-thymine: mp 89°–91° C.; $^1$H NMR (CDCl$_3$) δ1.94 (d, J=1.08 Hz, 3H, C-5 CH$_3$), 3.14 (s, 3H, SO$_2$CH$_3$), 3.25 (s, 3H, SO$_2$CO$_3$), 3.84 (s, 3H, CO$_2$CH$_3$), 4.55–4.70 (m, 3H, C-4'H and C-5'H), 5.25–5.31 (m, 2H, C-2'H AND C-3'H), 5.99 (d, J=3.27 Hz, 1H, C-1'H), 7.38 (m, 1H, C-6H) and 8.67 (broad, 1H, NH); $^{13}$C NMR (CDCl$_3$) δ12.49, 38.22, 38.52, 55.37, 63.94, 78.51, 79.47, 83.70, 88.23, 111.64, 134.70, 151,09, 155.13 and 163.90; TLC, R$_f$=0.58, silica gel, CHCl$_3$:CH$_3$OH/90:10.

Example A11

2,2'-Anhydro-3'-O-mesyl-5-O-(methoxycarbonyl)-1-β-D-lyxofuranosylthymine

A mixture of 2′,3′-di-O-mesyl-5′-O-(methoxycarbonyl)-1-β-D-xylofuranosyl thymine (4.00 g, 8.47 mmoles) from Example A10, and potassium carbonate (3.52 g, 25.4 mmoles) in acetonitrile (80 mL) was heated 4 h at reflux. The solution was filtered, salts washed with 2×50 mL portions of CHCl₃ and solvent removed by rotary evaporation affording 3.18 g (100%) of 2,2′-anhydro-3′-O-mesyl-5′-O-(methoxycarbonyl)-1-β-D-lyxofuranosylthymine as a white solid: mp 209°–211° C.; $^1$H NMR (DMSO-d₆) δ1.81 (d, J=1.07 Hz, 3H, C-5 CH₃), 3.35 (s, 3H, SO₂CH₃), 3.66 (s, 3H, CO₂CH₃), 3.96–4.40 (m, 2H, C-5′H), 4.63 (m, 1H, C-4′H), 5.53–5.70 (m, 2H, C-2′H and C-3′H), 6.19 (d, J=3.40 Hz, 1H, C-1′H) and 7.77 (m, 1H, C-6H); $^{13}$C NMR (DMSO-d₆) δ13.39, 37.64, 54.86, 64.80, 75.97, 77.03, 79.48, 88.75, 117.03, 131.83, 154.57, 159.42 and 171.21; TLC, R$_f$=0.21, silica gel, CHCl₃:CH₃OH/90:10.

Example A12

2′-Bromo-2′deoxy-3′-O-mesyl-5′-O-(methoxycarbonyl)-1-β-D-xylofuranosyl thymine

A mixture of 2,2′-anhydro-3′-O-mesyl-5′-O-(methoxycarbonyl)-1-β-D-lyxofuranosyl-thymine (0.50 g, 1.33 mmoles) from Example A11, lithium bromide (0.231 g, 2.66 mmoles) and sodium bisulfate monohydrate (0.184 g, 1.33 mmoles) in acetonitrile (15 mL) was heated 4.5 h at reflux. The solution was cooled to room temperature, diluted with chloroform, washed with water and solvent removed by rotary evaporation affording 0.561 g (93.4%) of 2′-bromo-2′-deoxy-3′-O-mesyl-5′-O-(methoxycarbonyl)-1-β-D-xylofuranosylthymine: mp 84°–88° C.; $^1$H NMR (CDCl₃) δ1.95 (d, J=1.23 Hz, 1H, C-5 CH₃), 3.11 (s, 3H, SO₃CH₃), 3.85 (s, 3H, CO₂CH₃), 4.47–4.81 (m, 4H, C-2′H, C-4′H and C-5′H), 5.27 (doublet of doublets, J=4.17 Hz and 3.24 Hz, 1H, C-3′H) 6.32 (d, J=3.84 Hz, 1H, C-1′H), 7.38 (q, J=1.23 Hz, 1H, C-6H) and 8.24 (broad, 1H, NH); $^{13}$C NMR (DMSO-d₆) δ12.06, 38.61, 48.77, 54.95, 64.91, 76.59, 82.01, 88.64, 109.98, 134.56, 150.37, 154.71 and 163.48; tlc, R$_f$=0.77, silica gel, CHCl₃:CH₃OH/90:10.

Example A13

1-[2-Deoxy-3-O-mesyl-5-O-methoxycarbonyl-β-D-threo-pentofuranosyl]-thymine

A flame dried 3-necked 100-mL round bottomed flask equipped with a nitrogen inlet, addition funnel and reflux condenser was charged with 2′-bromo-2′ deoxy-3′-O-mesyl-5′-O-(methoxycarbonyl)-1-β-D-xylofuranosylthymine (0.500 g, 1.09 mmoles) from Example A12 and toluene (50 mL). The solution was warmed to 85° C. and neat tributyltin hydride (0.500 g, 3.28 mmoles) was added dropwise over 1 minute. After approximately one third of the tributyltin hydride was added, a few crystals of azobisisobutyronitrile were added. The solution was heated at 85° C. for 90 minutes, cooled to room temperature and solvent removed by rotary evaporation. The residual oil was dissolved in acetonitrile (75 mL), the resulting solution washed with 3×75 mL portions of hexane and solvent removed by rotary evaporation affording 0.362 g (88.9%) of 1-[2-deoxy-3-O-mesyl-5-O-methoxycarbonyl-β-D-threopentofuranosyl]-thymine as a white crystalline solid: mp 70°–74° C.; $^1$H NMR (CDCl₃) δ1.95 (d, J=1.21, 3H, C-5 CH₃), 2.51–2.85 (m, 2H, C-2′H), 3.07 (s, 3H, SO₂CH₃), 3.82 (s, 3H, CO₂CH₃), 4.26–4.57 (m, 3H, C-4′ and C-5′H), 5.28 (m, 1H, C-3′H), 6.28 (doublet of doublets, J=7.63 and 3.88, 1H, C-1′H), 7.43 (m, 1H, C-6H) and 8.79 (broad, 1H, NH); $^{13}$C NMR (CDCl₃) δ12.58, 38.50, 39.33, 55.31, 64.26, 76.40, 79.16, 83.72, 111.48, 135.07, 150.58, 155.24 and 163.75; TLC, R$_f$0.51, silica gel, CHCl₃:CH₃OH/90:10.

Example A14

3′-Azido-3′-deoxy-5′-O-(methoxycarbonyl)thymidine

A mixture of 1-[2-deoxy-3-O-mesyl-5-O-methoxycarbonyl-β-D-threopentofuranosyl]-thymine (5.0 g, 13.2 mmoles) from Example A13 and sodium azide (1.07 g, 16.5 mmoles) in dimethylformamide (40 mL) was heated at 85°–90° C. for 4 h. The suspension was cooled to ambient temperature poured into 300 mL of water and the aqueous solution extracted with 3×100 mL portions of ethyl acetate. The combined organic extracts were washed with 2×100 mL portions of water and concentrated by rotary evaporation affording 3.88 g (90.2%) of 3′-azido-3′-deoxy-5′-O-(methoxycarbonyl)thymidine as a colorless oil: $^1$H NMR (CDCl₃) δ1.91 (d, J=1.15 Hz, 3H, C-5-CH₃), 2.30–2.49 (m, 2H, C-2′H), 3.83 (s, 3H, CO₂CH₃), 3.97–4.44 (m, 4H, C-3′H, C-4′H and C-5′H), 6.21 (t, J=6.26 Hz, 1H, C-1′H), 7.29 (q, J=1.15 Hz, 1H, C-6H) and 8.75 (broad, 1H, NH); $^{13}$C NMR (CDCl₃) δ12.42, 37.57, 55.28, 60.04, 66.39, 81.56, 84.94, 111.38, 135.28, 150.45, 155.18 and 164.03; TLC, R$_f$=0.78, silica gel, CHCl₃:CH₃OH/90:10.

Example A15

3′-Azido-3′-deoxythymidine

A mixture of 3′-azido-3′-deoxy-5′-O-(methoxycarbonyl)thymidine (2.50 g, 7.68 mmoles) from Example A14 and sodium bicarbonate (0.50 g) was heated 2.5 h at reflux in methanol (75 mL). The solvent was removed by rotary evaporation and the residual semi-solid was triturated with cold 5% aq. sodium bicarbonate (50 mL). The resulting solid was collected by filtration and dried in a vacuum oven at 55° C. for 17 h affording 1.71 g (83.4%) of 3′-azido-3′-deoxythymidine: mp 119°–121° C.; $^1$H NMR (DMSO-d₆) δ1.79 (d, J=1.04 Hz, 3H C-5 CH₃), 2.10–2.56 (m, 2H, C-2′H), 3.31–3.92 (m, 3H, C-3′ and C-5′H), 4.40 (m, 1H, C-4′H), 5.19 (t, J=5.22 Hz, 1H, OH), 6.11 (t, J=6.46 Hz, 1H, C-1′H), 7.68 (q, J=1.04, 1H, C-6H) and 10.65 (broad, 1H, NH); TLC R$_f$=0.35, silica gel, CHCl₃:CH₃OH/90:10.

I claim:

1. A compounds of formula (A)

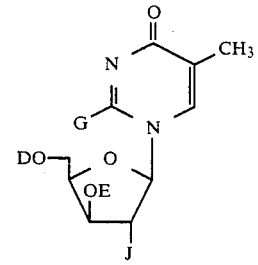

wherein D represents a methoxycarbonyl group, E represents a mesyl group and J represents a hydrogen atom, hydroxy group, an acetate or a trifluoromethyl benzoate group and G represents a hydroxy group or G and J together represent an —O— linkage between the 2 and 2′-positions of the compound of formula (A).

2. A compound of formula (B)

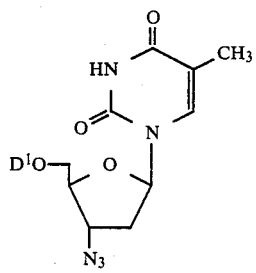

wherein D¹ represents a methoxycarbonyl group.

3. A compound which is represented by formula (C)

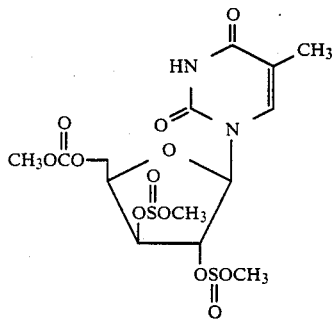

4. A compound which is represented by formula (D)

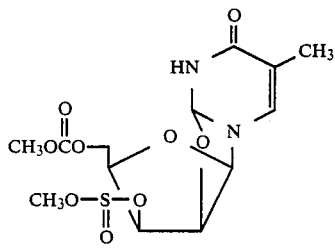

5. A compound which is represented by formula (E)

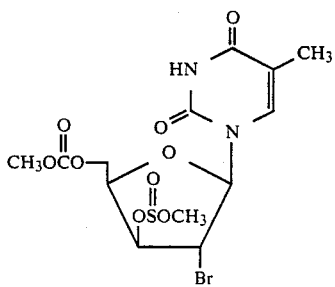

6. A compound selected from methyl 3-O-mesyl-5-O-(methoxycarbonyl)-2-O-(m-trifluoromethylbenzoyl)-D-xylofuranoside and 1-O-acetyl-3-O-mesyl-5-O-(methoxycarbonyl)-2-O-(m-trifluorobenzoyl)-D-xylofuranose.

* * * * *